(12) United States Patent
Khait et al.

(10) Patent No.: US 8,063,933 B2
(45) Date of Patent: Nov. 22, 2011

(54) BATTERY CONTACTS FOR AN IN-VIVO IMAGING DEVICE

(75) Inventors: Semion Khait, Tiberias (IL); Zvika Gilad, Haifa (IL); Chen Mann, Kibbutz Merhavia (IL)

(73) Assignee: Given Imaging Ltd., Yoqneam (IL)

( * ) Notice: Subject to any disclaimer, the term of this patent is extended or adjusted under 35 U.S.C. 154(b) by 1274 days.

(21) Appl. No.: 11/727,658

(22) Filed: Mar. 27, 2007

(65) Prior Publication Data

US 2007/0229656 A1    Oct. 4, 2007

Related U.S. Application Data

(60) Provisional application No. 60/785,992, filed on Mar. 27, 2006, provisional application No. 60/787,698, filed on Mar. 31, 2006.

(51) Int. Cl.
*A61B 1/00* (2006.01)

(52) U.S. Cl. .......................................................... 348/77

(58) Field of Classification Search ..................... 348/77
See application file for complete search history.

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |
| 5,993,378 A | 11/1999 | Lemelson | |
| 6,134,827 A * | 10/2000 | Jan ................................. | 43/124 |
| 6,240,312 B1 * | 5/2001 | Alfano et al. ................... | 348/77 |
| 7,009,634 B2 | 3/2006 | Iddan et al. | |
| 7,061,523 B2 * | 6/2006 | Fujita et al. ..................... | 348/77 |
| 7,505,802 B2 * | 3/2009 | Yoshino .......................... | 348/77 |
| 7,511,733 B2 * | 3/2009 | Takizawa et al. ............... | 348/77 |
| 7,570,301 B2 * | 8/2009 | Gilor ............................. | 348/373 |
| 7,643,865 B2 * | 1/2010 | Iddan et al. ..................... | 348/77 |
| 7,787,928 B2 * | 8/2010 | Frisch et al. .................... | 348/77 |
| 2002/0103417 A1 | 8/2002 | Gazdzinski | |
| 2003/0085994 A1 * | 5/2003 | Fujita et al. .................... | 348/77 |
| 2003/0117491 A1 * | 6/2003 | Avni et al. ...................... | 348/77 |
| 2003/0174208 A1 * | 9/2003 | Glukhovsky et al. .......... | 348/77 |
| 2005/0036059 A1 * | 2/2005 | Goldwasser .................... | 348/77 |
| 2005/0068416 A1 * | 3/2005 | Glukhovsky et al. .......... | 348/77 |

(Continued)

FOREIGN PATENT DOCUMENTS

DE    344 0177    5/1986

(Continued)

OTHER PUBLICATIONS

Panescu, D.;, "An imaging pill for gastrointestinal endoscopy," Engineering in Medicine and Biology Magazine, IEEE, vol. 24, No. 4, pp. 12-14, Jul.-Aug. 2005.*

(Continued)

*Primary Examiner* — Ajay Bhatia

(74) *Attorney, Agent, or Firm* — Pearl Cohen Zedek Latzer, LLP

(57) ABSTRACT

The invention provides an in vivo imaging device, the device comprising a first support having thereon a first battery contact, a second support having thereon a second battery contact, a battery disposed between the first support and the second support such that the battery is in contact with the first battery contact and with the second battery contact, wherein the first battery contact is a spring and the second battery contact comprises a pin to contact the battery and a housing for the pin and a battery stopper placed between the battery and the first or second support.

21 Claims, 15 Drawing Sheets

U.S. PATENT DOCUMENTS

2006/0004257 A1* 1/2006 Gilad et al. .................... 600/160
2007/0058036 A1* 3/2007 Shigemori et al. .............. 348/77

FOREIGN PATENT DOCUMENTS

| JP | 57-45833 | 3/1982 |
| JP | 4-109927 | 4/1992 |
| JP | 1992-144533 | 5/1992 |

OTHER PUBLICATIONS

Chao Hu; Max Qinghu Meng; Mandal, M.; , "Efficient magnetic localization and orientation technique for capsule endoscopy," Intelligent Robots and Systems, 2005. (IROS 2005). 2005 IEEE/RSJ International Conference on , vol., No., pp. 628-633, Aug. 2-6, 2005.*

U.S. Appl. No. 60/298,387, filed Jun. 18, 2001, Avni et al.

* cited by examiner

BATTERY CONTACTS FOR AN IN-VIVO IMAGING DEVICE

CROSS REFERENCE TO RELATED APPLICATIONS

This application claims the benefit of U.S. Provisional Application Ser. No. 60/785,992, filed on Mar. 27, 2006, and U.S. Provisional Application Ser. No. 60/787,698, filed on Mar. 31, 2006, which is/are incorporated in their entirety herein by reference.

FIELD OF THE INVENTION

The present invention relates generally to an in-vivo imaging system suitable for imaging the gastrointestinal (GI) tract or other body lumens. In particular, it is related to battery contacts for an in-vivo imaging device.

BACKGROUND OF THE INVENTION

Known devices may be helpful in providing in-vivo imaging. Autonomous in-vivo imaging devices, for example in-vivo imaging devices, such as swallowable or ingestible capsules or other devices may move through a body lumen, imaging as they move along. Some of these devices are battery operated and use a wireless connection to transmit image data.

In some in vivo devices, such as ingestible imaging capsules, the components within the capsule, such as a battery contact(s), may be arranged on a board or on several boards, for example on a printed circuit board (PCB). In some cases the boards are aligned along an axis of the capsule and are electrically connected by one or more wires.

During the movement of the in-vivo imaging device within and outside a human body, the in-vivo imaging device may endure conditions such as turbulence, vibrations and temperature changes. Such occurrences may cause disconnection between contacts, such as battery contacts, battery and/or electrical circuits or electrical components of the in-vivo imaging device.

There is a need for a battery contact(s) that will be able to withstand turbulence and acute conditions and will enable continuous and constant contact between the battery and electric components of the imaging device in the course of the device movement both within and outside a human body.

SUMMARY OF THE INVENTION

The present invention provides, according to some embodiments, an in vivo imaging device comprising a circuit board, for example a flexible circuit board and/or a circuit board having one or more rigid sections or portions, and one or more flexible sections or portions.

According to one embodiment of the present invention, an example for economizing space usage may be by employing battery contacts configured to occupy a minimum of space within the in-vivo imaging device and circuit board. For example, according to one embodiment of the present invention a rigid section of a circuit board may support both a transmitter/receiver and a battery contact, and thus decrease the number of rigid and flexible sections of the circuit board. Efficient and economized circuit board setup may enable circuit board folding into smaller sizes which may take up less space, and thus may provide for smaller sized in-vivo devices or for more usable space within an in vivo device.

According to some embodiments of the present invention, the in vivo imaging device may include one or more imagers. The device may further include an illumination source(s), an optical system, a switch, one or more battery contacts a transmitter/receiver and an antenna for transmitting image data to a receiving system. According to one embodiment the transmitter is a wireless transmitter. According to some embodiments the transmitter may be a transceiver configured to accept signals transmitted from an external source.

According to some embodiments of the present invention, the battery contacts include, for example a push-button contact, a 'pin button and spring' contact or a spring biased plunger contact, a wire or a thin-sheet strip or other suitable battery contact. According to some embodiments the battery contacts may be integrated or embedded, for example, within a rigid portion and/or the flexible portion of the circuit board. According to some embodiments of the present invention the battery contact may be combined with or attached to other elements in the in vivo imaging device so as to possibly reduce the amount of space taken up by it.

BRIEF DESCRIPTION OF THE DRAWINGS

The invention is herein described, by way of example only, with reference to the accompanying drawings, in which like components are designated by like reference numerals, wherein.

Figure 1:
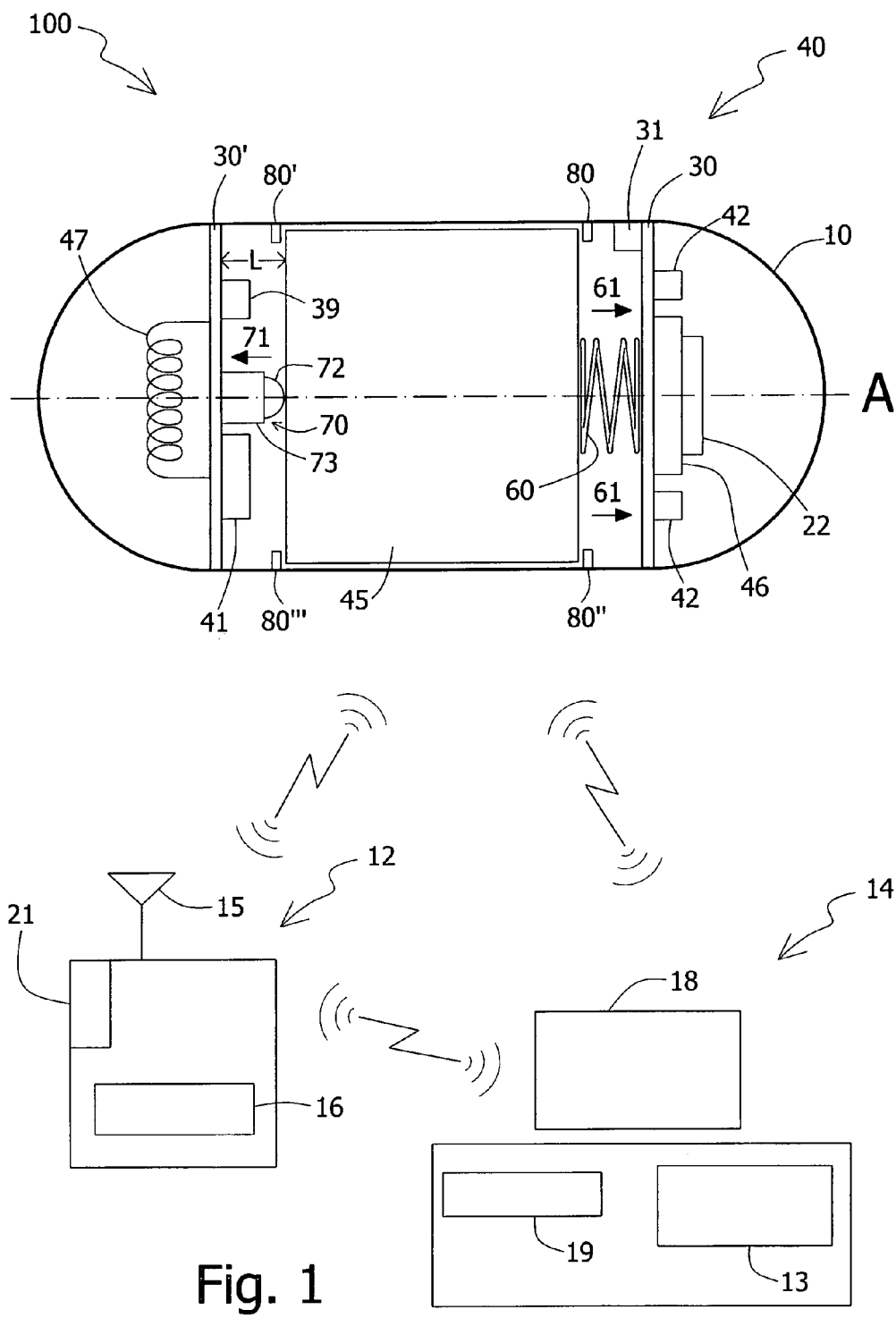
FIG. 1 schematically illustrates an in vivo imaging device and system, according to one embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Reference is made to FIG. 1, which shows a schematic diagram of an in-vivo imaging system 100 according to one embodiment of the present invention. The in-vivo imaging system 100 may include an in-vivo imaging device 40 having, for example an imager 46, for capturing images, an optical system 22, an illumination source(s) 42 such as white LEDs (Light Emitting Diode), OLEDs (Organic LED) or other illumination sources, for illuminating the body lumen, a power source such as a battery 45 or battery pack, for powering device 40, a switch 39 such as a magnetic switch, such as a MEMS switch, for example, MEMSCAP MEMS Switch or a REED Switch, for example, a RI-80 SMD switch, and a transmitter/receiver 41, typically integrated on an ASIC, with antenna 47, for transmitting and/or receiving in-vivo data e.g. raw data or images, for example to or from an external device such as a receiver/recorder 12. According to one embodiment, the device 40 may include one or more supports, such as two separated PCBs (Printed Circuit Board) 30 and 30', or a single PCB such as flexible circuit board or a rigid-flex circuit board. According to one embodiment of the present invention, the various components of the device 40, such as the illumination source(s) 42, the transmitter/receiver 41, the switch 39, the antenna 47 and the imager 46 may be disposed on a support, for example the PCBs 30 or 30'.

In some embodiments, imager 46 may include, for example, a CCD (Charge Coupled Device) camera or imager, a CMOS (Complementary Metal Oxide Semiconductor) camera or imager, a digital camera, a video camera, or other suitable imagers, cameras, or image acquisition components. According to some embodiments a 320×320 pixel imager may be used. Pixel size may be between 5 to 6 micron. According to some embodiments pixels may be each fitted with a micro lens. Other imagers are possible.

Transmitter/receiver 41 may operate using radio waves; but in some embodiments, such as those where device 40 is or is included within an endoscope, transmitter/receiver 41 may transmit data via, for example, a wire, optical fiber and/or other suitable methods. Other suitable methods or components for wired or wireless transmission may be used.

In one embodiment, all of the components may be sealed within the device body or housing 10 (the body or shell may include more than one piece); for example, the imager 46, the optical system 22, the illumination sources 42, the battery 45, the transmitter/receiver 41, the switch 39, and the antenna 47 may all be sealed or enclosed within the device housing 10.

In some embodiments of the present invention, in-vivo device 40 may include one or more sensors 31 other than and/or in addition to imager 46, for example, temperature sensors, pH sensors, pressure sensors, blood sensors, etc. In some embodiments of the present invention, device 40 may be an autonomous device, a capsule, or a swallowable capsule. In other embodiments of the present invention, device 40 may not be autonomous, for example, device 40 may be an endoscope or other in-vivo imaging sensing device.

According to some embodiments of the present invention the in-vivo imaging device 40 may include one or more battery contacts for power source(s) such as battery 45. For example device 40 may include two battery contacts, for example two different types of battery contacts such as battery contact 60, which may be attached for example to the PCB 30, and battery contact 70 which may be attached for example to the PCB 30'. The battery contact 60 may be for example a spring while battery contact 70 may be a push-button contact such as a 'pin button and spring' contact or a spring based plunger contact. In some embodiments the battery 45 (or a plurality of batteries) may be sandwiched between the two battery contacts 60 and 70. For example the battery 45 may be pressed by the two battery contacts 60 and 70 along latitude axis A. In some embodiments battery contact 60 may be pressed in a direction 61 into the PCB 30 and battery contact 70 may be pressed in a direction 71 into the PCB 30'.

According to some embodiments of the present invention the battery contact 70 may include a button or pin 72 and a housing 73 such as a spring housing. In some embodiments the pin 72 may be pressed into the housing 73 such that a space L, for placing components of device 40, may be formed between the battery 45 and the PCB 30'. For example, the battery contact 70 may be placed at the center of PCB 30' and may form a space L so that transmitter/receiver 41 and switch 39 may be placed between the PCB 30' and the battery 45.

According to some embodiments of the present invention the device 40 may include one or more stoppers such as battery pack stoppers 80, 80', 80" and 80'". The battery stoppers 80, 80', 80" and 80'" may be used to prevent excessive pressure on components of the device 40, such as components which may be placed in close proximity to the battery 45, for example the PCBs 30 and 30' or components which are placed between the battery 45 and the PCBs 30 and 30' e.g. transmitter/receiver 41 and switch 39. In some embodiments, the battery stoppers may be attached to or may be part of the housing 10.

Devices according to embodiments of the present invention, including imaging, receiving, processing, storage and/or display units suitable for use with embodiments of the present invention, may be similar to embodiments described in U.S. Pat. No. 5,604,531 to Iddan et al., entitled IN-VIVO VIDEO CAMARA SYSTEM, and/or in U.S. Pat. No. 7,009,634 to Iddan et al., issued Mar. 7, 2006 entitled A DEVICE AND SYSTEM FOR IN-VIVO IMAGING, both of which are assigned to the common assignee of the present invention and which are hereby incorporated by reference. Of course, devices and systems as described herein may have other configurations and other sets of components.

The in-vivo imaging device 40 may, according to some embodiments of the present invention, transmit information e.g., images or other data to the receiver/recorder 12 which is possibly close to or worn on a subject. The receiver/recorder 12 may include an antenna or antenna array 15 and a data storage unit or memory 16. The receiver/recorder 12 may of course take other suitable configurations and may not include an antenna or antenna array. In some embodiments of the present invention, the data receiver/recorder 12 may, for example, include processing power and/or a LCD display for displaying image data.

According to some embodiments of the present invention, the receiver/recorder 12 may, for example, transfer the received data to a computing device 14, such as a workstation or personal computer, where the in-vivo raw data may be further analyzed, stored, and/or displayed to a user. Computing device 14 may typically be a personal computer or workstation, which may include standard components such as a processing unit 13, a memory, for example storage 19, a disk drive, a monitor 18, and input-output devices, although alternate configurations are possible. Monitor 18 may be a conventional video display, but may, in addition, be any other device capable of providing image, stream of images or other data. Instructions or software for carrying out a method according to an embodiment of the invention may be included as part of computing device 14, for example stored in storage 19. In some embodiments, the receiver/recorder 12 may include a link 21 such as for example a USB, blue-tooth, radio frequency or infra-red link, that may connect to antenna 15 or to a device attached to antennas 15.

Figure 2A:
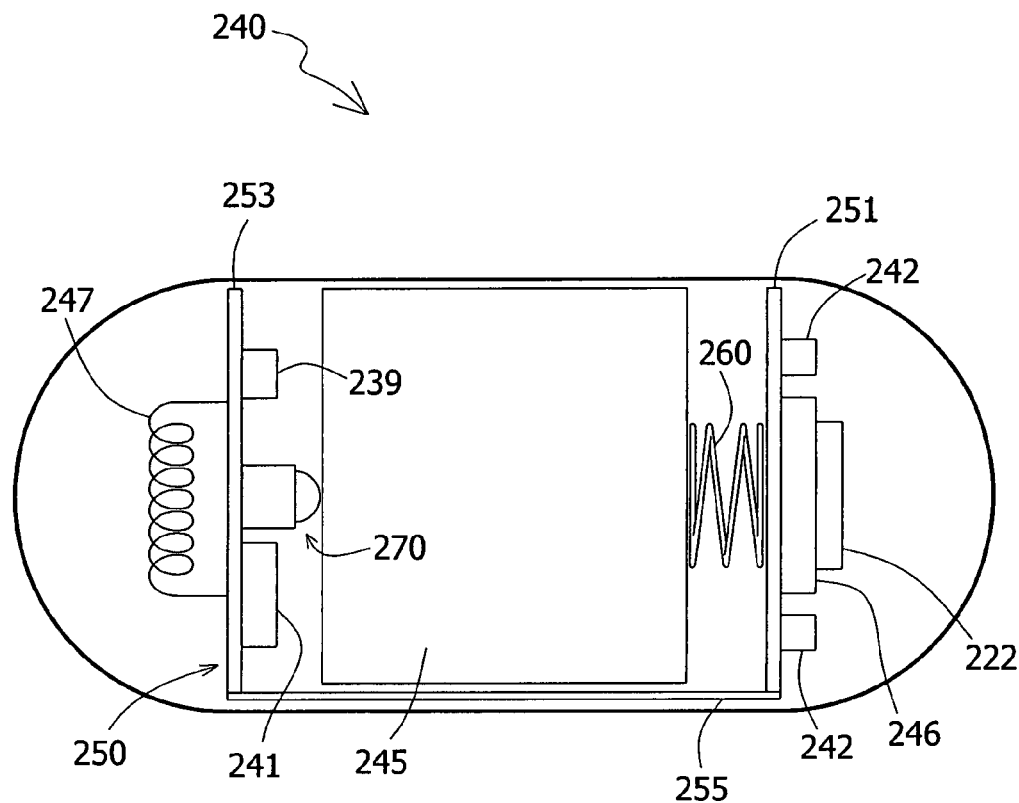
FIG. 2A schematically illustrates an in vivo imaging device, according to another embodiment of the present invention.

FIG. 2A schematically illustrates an in vivo imaging device 240 according to some embodiments of the present invention. According to one embodiment of the present invention, the various components of the device 240 may be disposed on a circuit board 250 including rigid and flexible portions; preferably the components are arranged in a stacked vertical fashion, however other arrangements are possible. For example, rigid portion 251 of the circuit board 250 may hold an imager 246, an optical system 222 and illumination source(s) 242, while rigid portion 253 may hold an antenna 247. According to one embodiment of the present invention, the other side of the rigid portion 251 may include, for example, a battery contact 260, while the other side of rigid portion 253 may include a transmitter/receiver 241 a switch 239 and a battery contact 270. The rigid portions, e.g. portions 253 and 251, of the circuit board 250 may be connected, for example by a flexible portion 255. In some embodiments, each rigid portion of the circuit board 250, e.g. portions 253 and 251, may include two rigid sections; sandwiched between the rigid sections is a flexible portion 255 of the circuit board for connecting the rigid portions 253 and 251. In alternate embodiments, other arrangements of components may be placed on a circuit board having rigid portions connected by flexible portions.

In alternate embodiments, a circuit board having rigid portions and flexible portions may be used to arrange and hold components in other in vivo sensing devices, such as a swallowable capsule measuring pH, temperature or pressure, or in a swallowable imaging capsule having components other than those described above. Such circuit boards may be similar to embodiments described in U.S. application Ser. No. 10/879,054 entitled IN VIVO DEVICE WITH FLEXIBLE CIRCUIT BOARD AND METHOD FOR ASSEMBLY THEREOF, and U.S. application No. 60/298,387 entitled IN VIVO SENSING DEVICE WITH A CIRCUIT BOARD HAVING RIGID SECTIONS AND FLEXIBLE SECTIONS, each incorporated by reference herein in their entirety.

According to one embodiment of the present invention, the circuit board 250 may be folded, for example, as shown in FIG. 2A. When folded, the battery contacts 260 and 270 may contact a set of one or more batteries, e.g., battery 245, which may be sandwiched between the two rigid circuit board portions 251 and 253. The circuit board 250 may be folded in various manners. For example, FIG. 2A schematically shows a circuit board, according to an embodiment of the invention, arranged as a "C" with rigid portions 251 and 253 and a flexible portion 255.

According to some embodiments of the present invention, the battery contacts 260 and 270 may be formed, manufactured or produced as an integrated or integral part of circuit board 250 or rigid portions 251 and 253. For example, a process of manufacturing circuit board 250 or rigid portions 251 and 253 may include bonding, gluing, soldering, connecting, or otherwise firmly attaching battery contacts 260 and 270 as a part of circuit board 250. Such manufacturing may result in a pre-provided circuit board 250 or rigid portions 251 and 253 having, for example battery contacts 260 and 270 integrated therein, and may eliminate the need to assemble or further connect the battery contacts 260 and 270 to the circuit board 250 or rigid portions 251 and 253, after the manufacturing process of circuit board 250 or rigid portions 251 and 253 is completed.

Figure 2B:
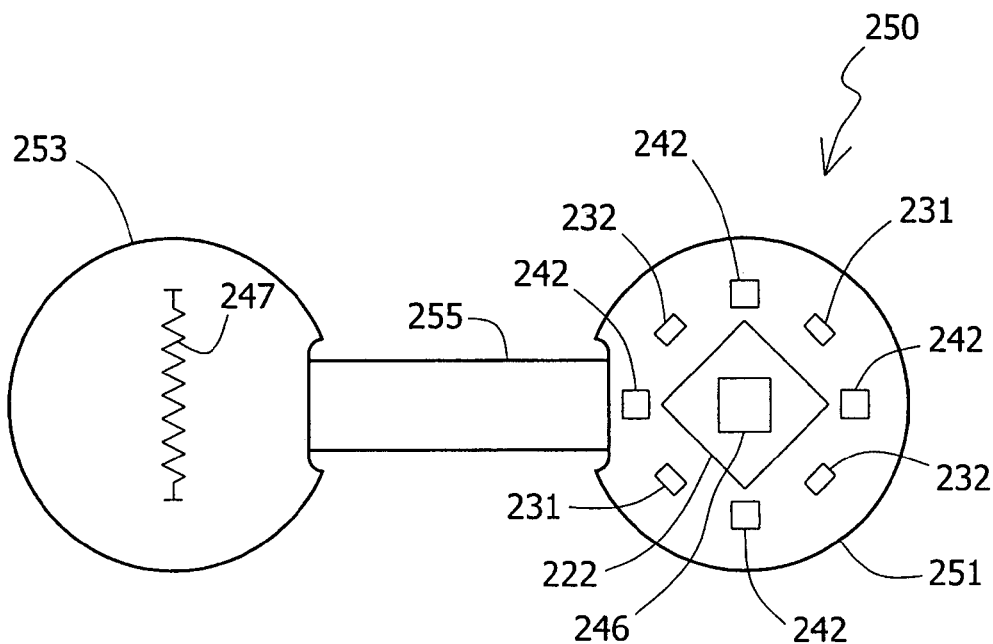
FIGS. 2B and 2C schematically illustrate a top view and a bottom view, respectively, of a circuit board in accordance with some embodiments of the present invention.
Figure 2C:
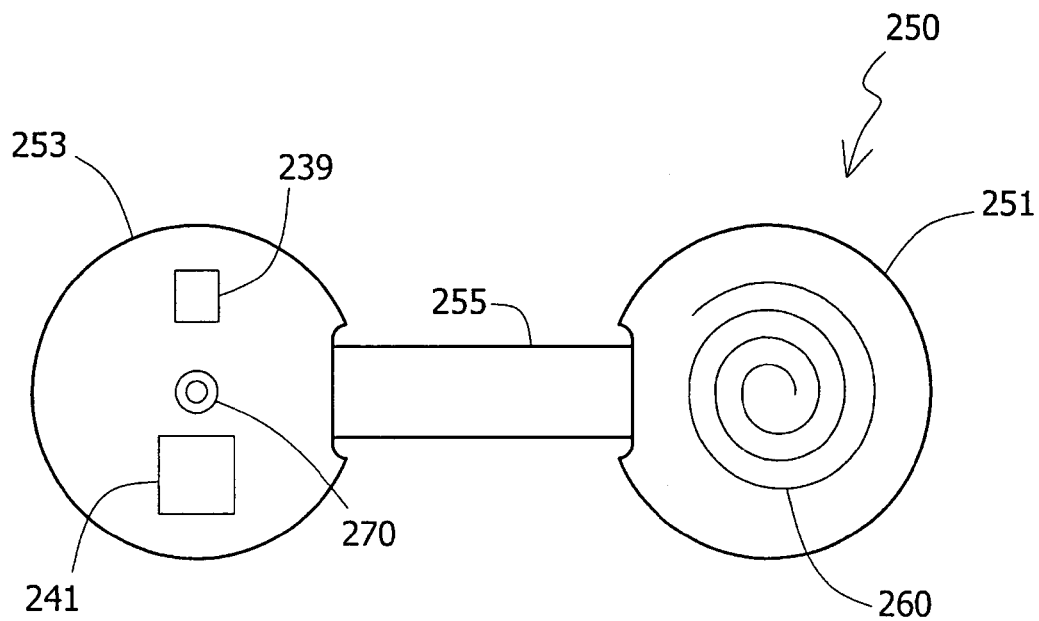
Figure 2D:
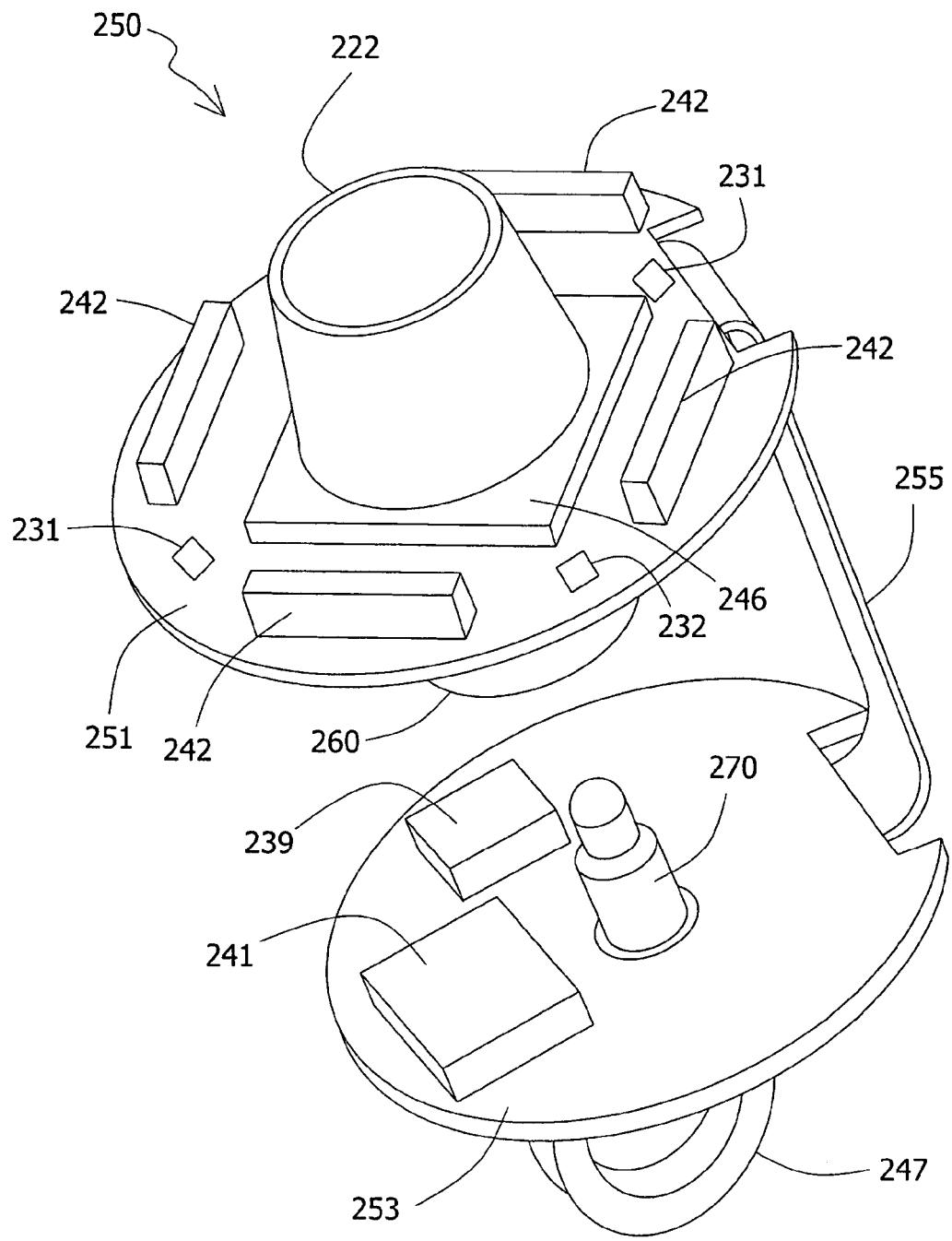
FIG. 2D schematically illustrates a three-dimensional view of a circuit board and a battery contact, in accordance with some embodiments of the present invention.

Reference is now made to FIGS. 2B-2D, which are a top view a bottom view and a three-dimensional view, respectively, of a battery contact 270, configured to occupy a minimum of space within device 240, attached to a circuit board e.g. circuit board 250, according to some embodiments of the present invention. In some embodiments, circuit board 250 may be used in conjunction with device 240 of FIG. 2A, or with other suitable devices and systems for in vivo sensing or in vivo imaging. Circuit board 250 may include, for example, one or more rigid portions and one or more flexible portions. For example, circuit board 250 may include rigid portions 251 and 253, which may be interconnected using flexible portion 255. Although two rigid portions and one flexible portion are shown, embodiments of the present invention are not limited in this regard, and may include other numbers, orders or combinations of rigid portions and/or flexible portions. In some embodiments, rigid portion 251 may include, for example, one or more illumination sources 242, and optionally one or more resistors 231 and/or capacitors 232 to regulate or control the power provided to illumination sources 242. In some embodiments, rigid portion 251 may include an imager 246 an optical system 222 and a battery contact 260 e.g., a spring able to hold the battery 245 in place. In some embodiments, rigid portion 253 may include an antenna 247, a battery contact 270, a transmitter/receiver 241 and a switch 239. According to some embodiments of the present invention, battery contact 270 may be attached to the center of rigid section 235 in order to prevent side pressure on the battery 245 or the rigid sections 251 and 253. Although one imager 246 is shown, embodiments of the invention are not limited in this regard; for example, in one embodiment, circuit board 250 may include two imagers, or another suitable number of imagers. The flexible portion 255 of circuit board 250 may allow bending, folding, twisting or positioning of circuit board 250 into certain shapes. For example, circuit board 250 may have a "C" shape, or other suitable shapes.

Figure 3A:
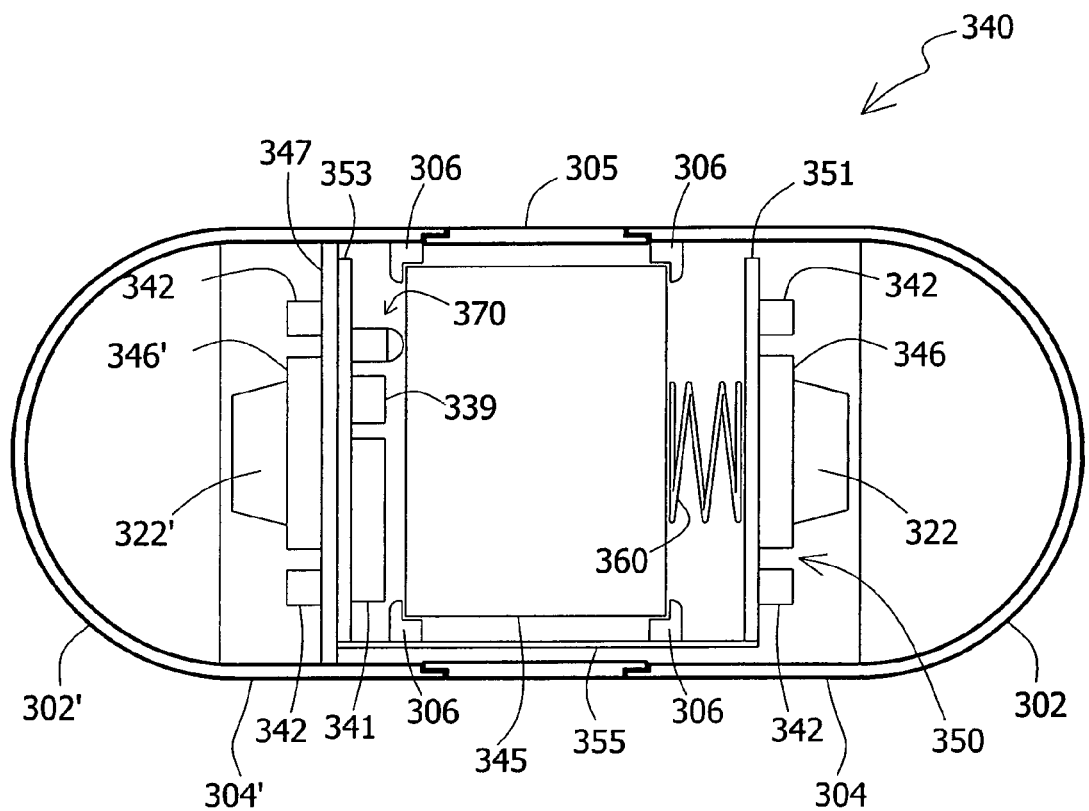
FIG. 3A schematically illustrates an in vivo imaging device, according to another embodiment of the present invention.

Another embodiment of the present invention is schematically illustrated in FIG. 3A, in which a longitudinal cross section of device 340 is schematically shown. According to one embodiment of the present invention, device 340 may include two optical domes 302 and 302'. According to one embodiment of the present invention each optical dome 302 and 302' may be an integral part of two elongated heads, such as a transparent front head 304 and a transparent rear head 304'. According to one embodiment of the present invention the front and rear heads 304 and 304' may be connected to a connecting sleeve, for example an opaque sleeve 305. The sleeve 305 may include one or more battery stoppers, such as stoppers for holding the power sources, e.g. battery 345, of an in-vivo imaging device such as device 340. According to some embodiments of the present invention behind the transparent heads 304 and 304' may be, respectively, situated for example an illumination sources 342, two optical systems 322 and 322', two imagers 346 and 346' a transmitter/receiver 341 and a switch 339 and an antenna 347. The device 340 may further include one or more power sources such as battery 345, which may provide power to the entirety of electrical elements of the device 340, and one or more battery contacts such as battery contacts 360 and 370 for electrically connecting the electrical elements of the device 340 to the battery 345.

In some embodiments battery contact 360 may be for example a spring while battery contact 370 may be for example a push-button contact a 'pin button and spring' contact or a spring biased plunger contact. According to some embodiments of the present invention, device 340 is capable of simultaneously obtaining images of the body lumen, for example, the GI tract, from two ends of the device. For example, according to one embodiment of the present invention device 340 may be a floatable capsule having a front end and a rear end, which is capable of passing the entire GI tract.

According to one embodiment of the present invention, the various components of the device 340 may be disposed on a circuit board 350 including rigid and flexible portions; preferably the components are arranged in a stacked vertical fashion. For example, rigid portion 351 of the circuit board 350 may hold the imager 346, the optical system 322, and the illumination sources 342 while rigid portion 353 may hold the imager 346', the optical system 322' the antenna 347 and the illumination sources 342. According to one embodiment of the present invention, the other side of the rigid portion 353 may include, for example a transmitter/receiver 341 a switch 339, and the battery contact 370. According to some embodiments of the present invention the battery contact 370 may be placed at the sides of the rigid portion 353, to enable the attachment of components such as the switch 339 or the transmitter/receiver 341 which occupy large space within the device 340. The other side of rigid portion 351 may hold the battery contact 360. According to some embodiments of the present invention, each rigid portion of the circuit board may be connected to another rigid portion of the circuit board by a flexible portion 355 of the circuit board 350.

Figure 3B:
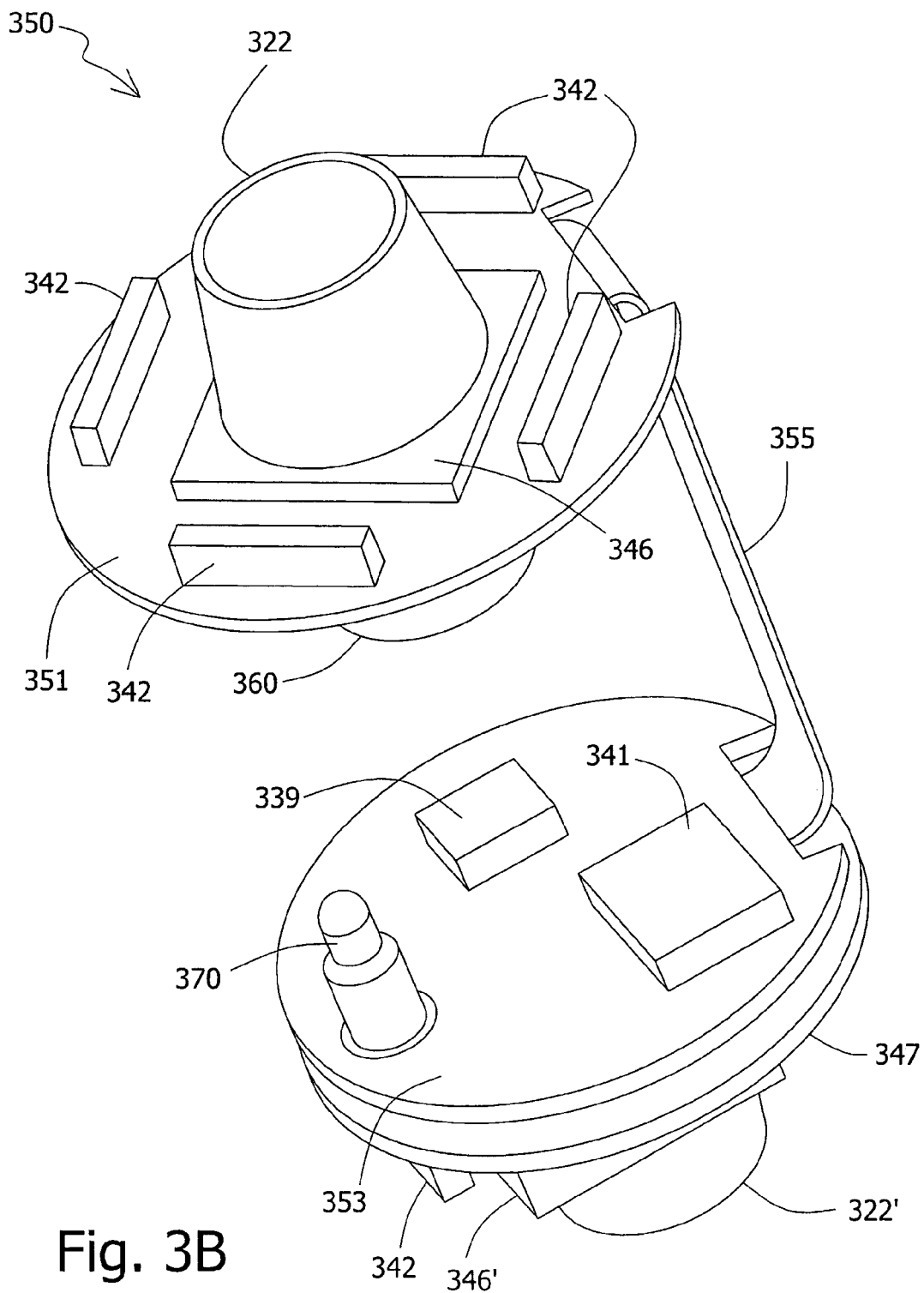
FIG. 3B schematically illustrates a three-dimensional view of a circuit board and a battery contact, in accordance with some embodiments of the present invention.

FIG. 3B schematically illustrates a three-dimensional view of a circuit board 350 and a battery contact 370 configured to occupy a minimum of space within device 340, in accordance with some embodiments of the invention. Circuit board 350 may include, for example, one or more rigid portions and one or more flexible portions. For example, circuit board 350 may include rigid portions 351 and 353, which may be interconnected using a flexible portion 355. Although two rigid portions and one flexible portion are shown, embodiments of the invention are not limited in this regard, and may include other numbers, orders or combinations of rigid portions and/or flexible portions.

According to one embodiment of the present invention, rigid portion 351 may have mounted on it on one side an imager 346, an optical system 322 and one or more illumination sources 342; the other side of the rigid portion 351 may include a battery contact 360 such as a spring and possibly other components. Rigid portion 353 may include an imager 346', an optical system 322', one or more illumination sources 342 and an antenna 347 on one side; the other side of the rigid portion 353 may include, for example a switch 339, a transmitter/receiver 341 and a battery contact 370. According to some embodiments, as shown in FIG. 3B the battery contact 370, may be placed at the sides of the rigid portion 353 e.g. at the edge of the rigid section 353 in front of the flexible portion 355, to enable the attachment of components such as the switch 339 or the transmitter/receiver 341 which may occupy a relatively large space within the device 340.

Figure 3C:
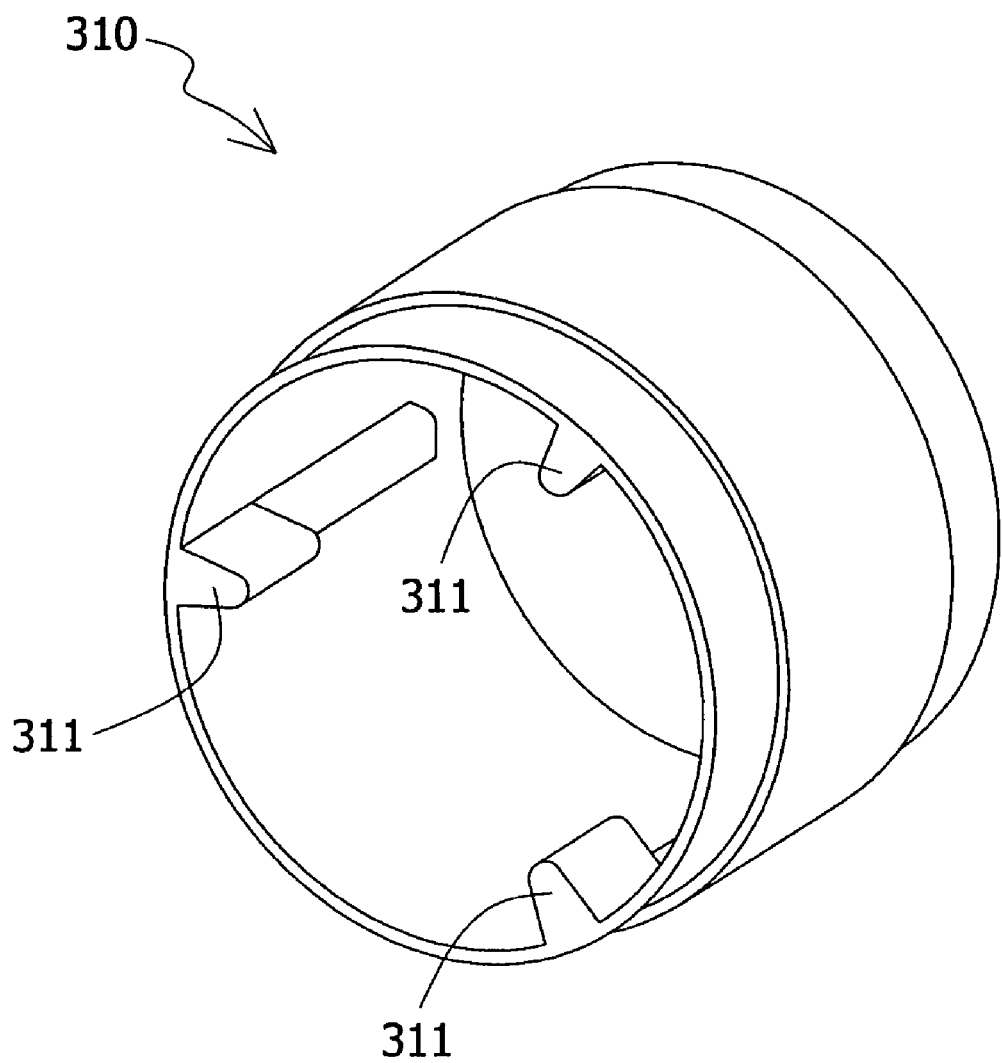
FIG. 3C schematically illustrates a three-dimensional view of a connecting sleeve, in accordance with some embodiments of the present invention.

Reference is now made to FIG. 3C which schematically illustrates a three-dimensional view of a connecting sleeve such as a sleeve 310, according to some embodiments of the present invention. In some embodiments, sleeve 310 may be an example of sleeve 305 of FIGS. 3A. In some embodiments, sleeve 310 may be used in conjunction with device 40 of FIG. 1, or with other suitable devices and systems for in vivo sensing or in vivo imaging.

According to one embodiment of the present invention sleeve 310 may include one or more stoppers, such as battery stoppers for holding the power sources, e.g. battery 345, of an in-vivo imaging device such as device 340. The battery stoppers may be used to prevent 'too much' pressure, or side pressure on components of the device 340, such as the battery 345 and components which are located in close proximity to the battery 345, for example the circuit board 350 or components which are placed between the battery 345 and the rigid sections 353 and 351 e.g. transmitter/receiver 341 and switch 339. In some embodiments, sleeve 310 may include three battery stoppers, such as battery stoppers 311 which may be attached or may be integrated part for example of the inside section of sleeve 310.

Figure 4:
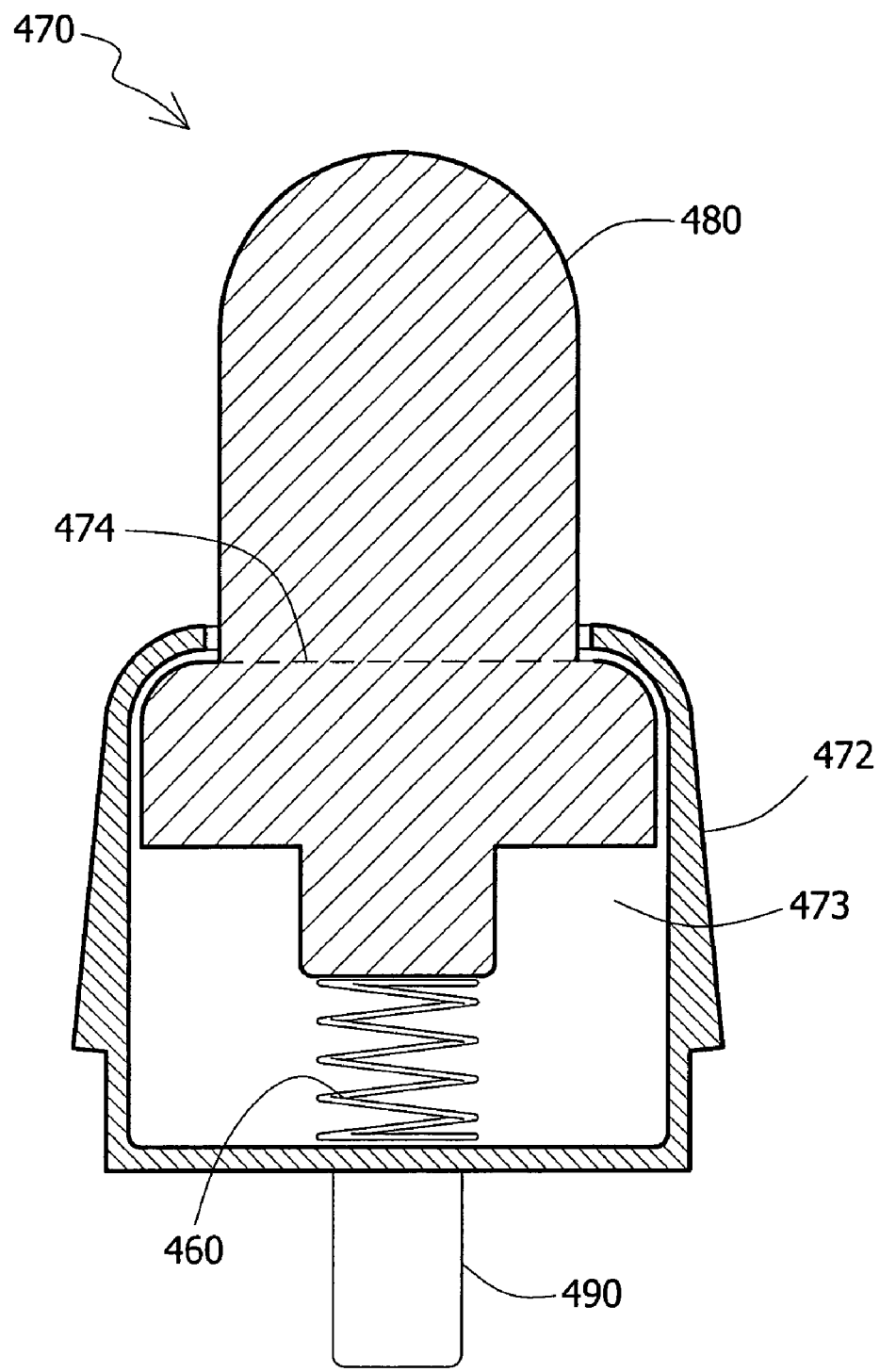
FIG. 4 schematically illustrates a battery contact, in accordance with some embodiments of the present invention.

Reference is now made to FIG. 4, which is a schematic diagram illustrating a battery contact 470 of an in-vivo imaging device such as device 40, according to some embodiments of the present invention. In some embodiments, battery contact 470 may be an example of battery contact 270 of FIGS. 2A-2D or battery contact 370 of FIGS. 3A-3C. In some embodiments, battery contact 470 may be used in conjunction with device 40 of FIG. 1, or with other suitable devices and systems for in vivo sensing or in vivo imaging.

According to one embodiment, the battery contact 470 may include a pin 480 e.g. a plunger or a push button which may contact for example a terminal of a power source such as the battery 45, the pin 480 may be made of stainless steel and/or a conductive coating e.g. gold plating. The battery contact may further include a housing such as a spring housing 472 a spring 460 and a connection portion 490 for electrically connecting the battery contact 470 to a support such as circuit board 50.

Figure 5A:
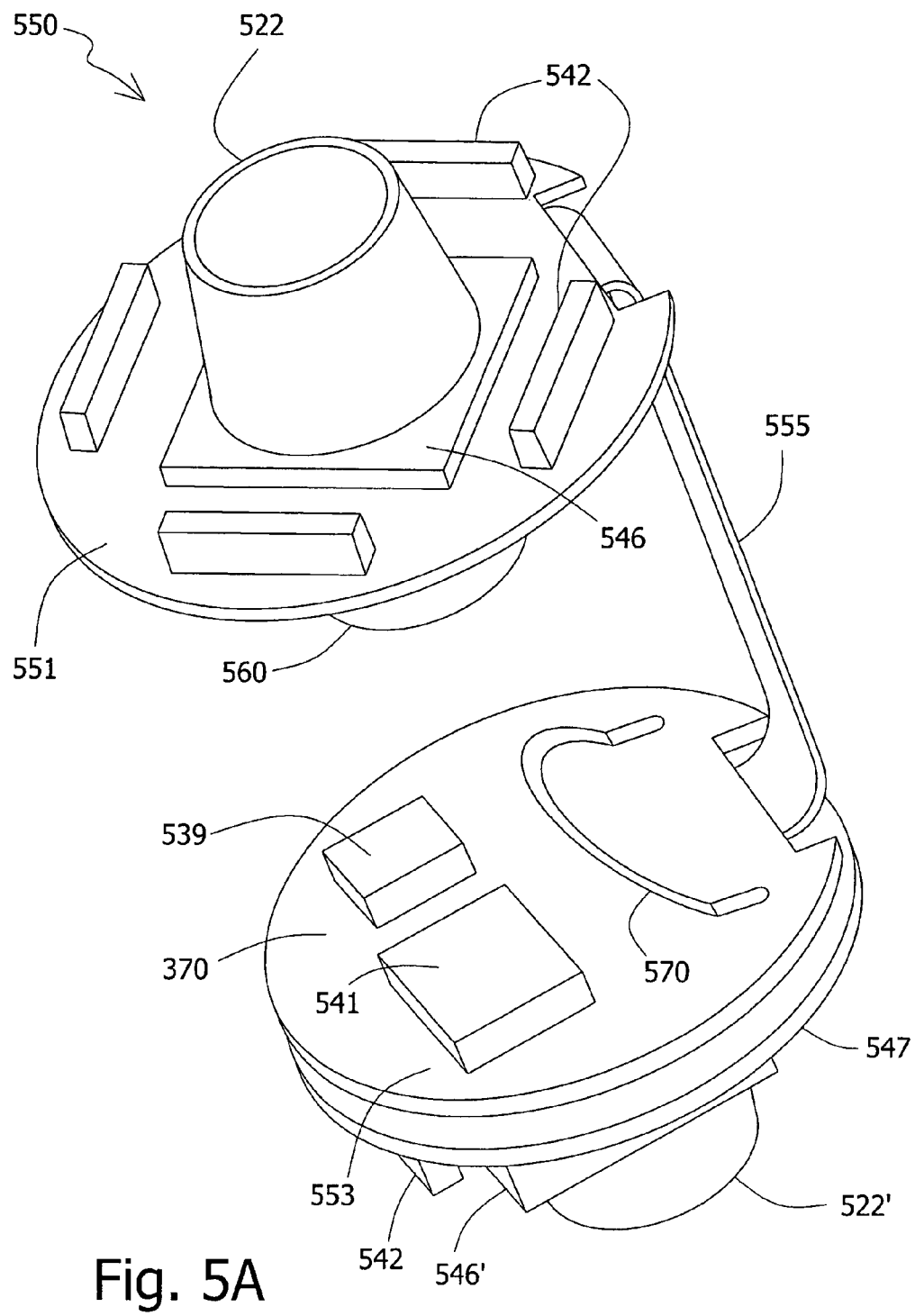
FIG. 5A schematically illustrates a three-dimensional view of a circuit board and a battery contact, in accordance with some embodiments of the present invention.
Figure 5B:
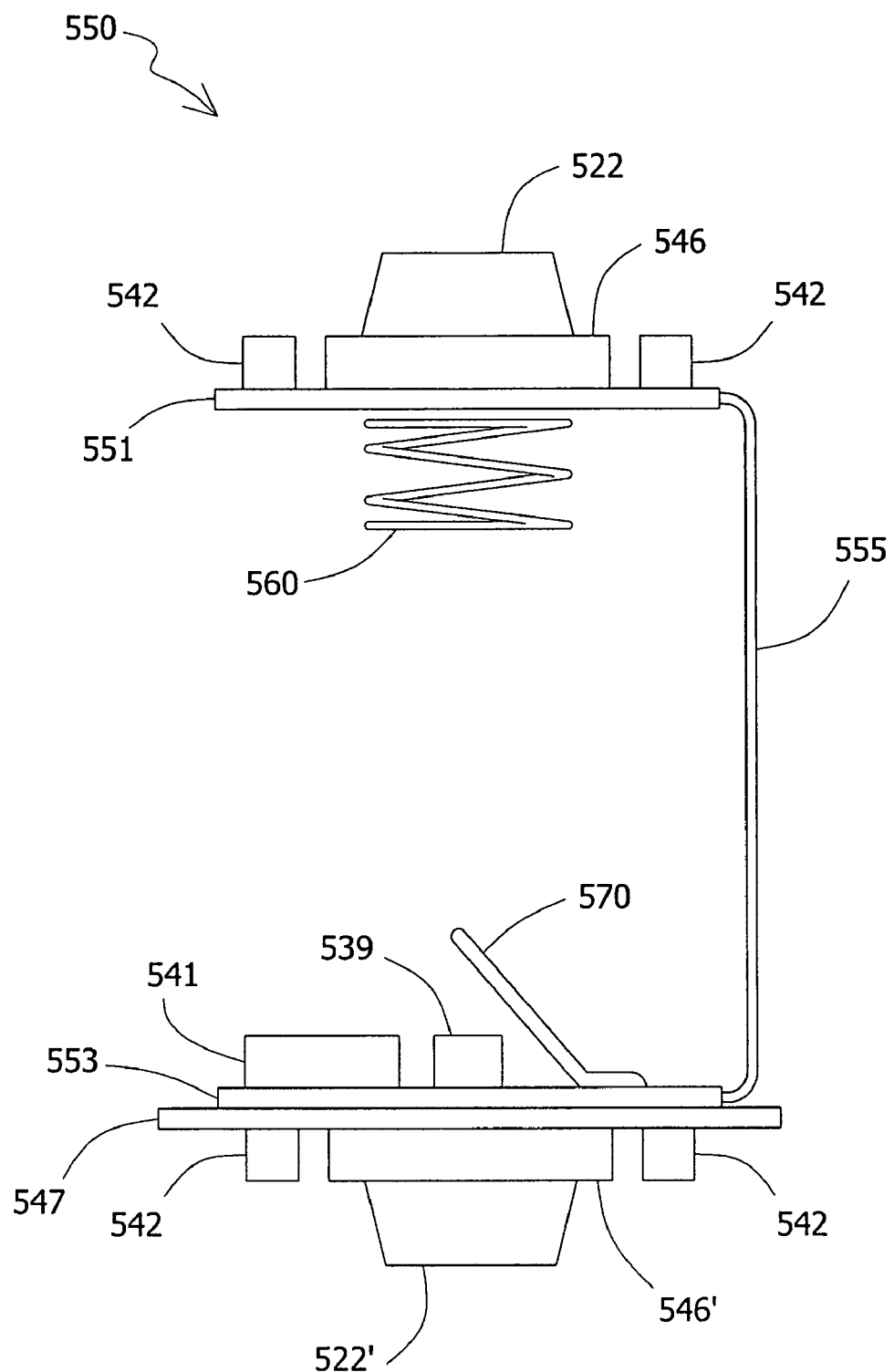
FIG. 5B schematically illustrates a side view of a circuit board and a battery contact, in accordance with some embodiments of the present invention.

FIGS. 5A and 5B schematically illustrate a three-dimensional view and a side view, respectively, of a circuit board 550 and a battery contact 570 configured to occupy a minimum of space, within an in-vivo imaging device, in accordance with some embodiments of the present invention. In some embodiments, circuit board 550 may be used in conjunction with device 340 of FIG. 3A, or with other suitable devices and systems for in vivo sensing or in vivo imaging. Circuit board 550 may include, for example, one or more rigid portions and one or more flexible portions. For example, circuit board 550 may include rigid portions 551 and 553, which may be interconnected using a flexible portion 555. Although two rigid portions and one flexible portion are shown, embodiments of the invention are not limited in this regard, and may include other numbers, orders or combinations of rigid portions and/or flexible portions.

According to one embodiment of the present invention, rigid portion 551 may have mounted on it on one side an imager 546, an optical system 522 and one or more illumination sources 542; the other side of the rigid portion 351 may include a battery contact 560 such as a spring and possibly other components. Rigid portion 553 may have mounted on it on one side an imager 546', an optical system 522' one or more illumination sources 542 and an antenna 547; the other side of the rigid portion 553 may include, for example a switch 539, a transmitter/receiver 541 and a battery contact 570. According to some embodiments, the battery contact 570 may be a wire, a spring wire or a thin-sheet strip and may be placed for example in close proximity or over components of the device 40 such as the switch 539 and/or the transmitter/receiver 541.

Figure 5C:
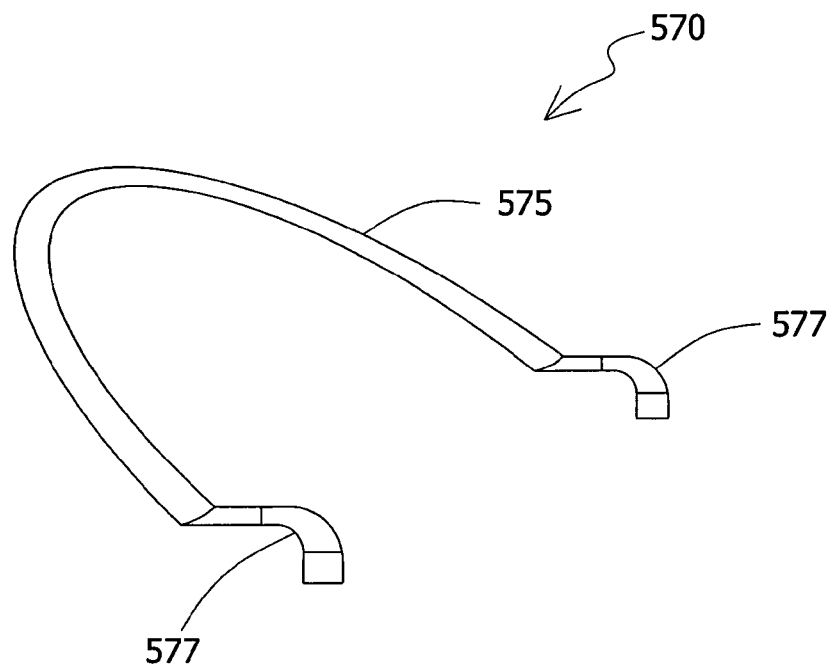
FIG. 5C schematically illustrates a three-dimensional view of a battery contact, in accordance with some embodiments of the present invention.
Figure 5D:
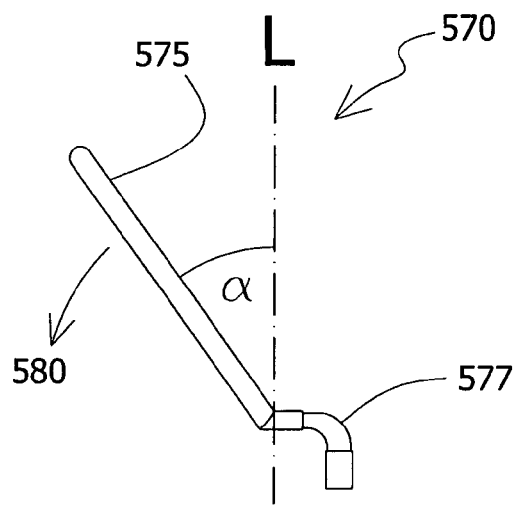
FIG. 5D schematically illustrates a side view of a battery contact, in accordance with some embodiments of the present invention.

FIGS. 5C and 5D schematically illustrate a three-dimensional view and a side view, respectively, of a battery contact 570, in accordance with some embodiments of the present invention. According to one embodiment, the battery contact 570 may be a coiled battery contact and may include for example a spring wire portion 575. The portion 575 may be a half ring, arc, or crescent shaped and may be made of stainless steel and a conductive coating e.g. gold plating. Typically, the battery contact 570 has compatible measurements and weight for a suitable incorporation into a circuit board of an in-vivo imaging device, for example into the rigid portion 553. For example, the battery contact 570 may be made of stainless steel and may be of a thickness of about 0.2 mm. The battery contact 570 may include one or more connection portions e.g. portions 577, for connecting the battery contact 570, for example by soldering, to a support such as a circuit board e.g. circuit board 550.

According to some embodiments of the present invention, as shown in FIG. 5D, the portion 575 may be shifted at an angle α (in relation to a longitudinal axis L) in some embodiments a may be between 0 and 90 degrees. In operation, a support such as circuit board 550 may be folded around a power source such as battery 345. The battery 345 may press the battery contact 570 such that portion 575 may be shifted in a direction 580 e.g. towards rigid portion 553 of circuit board 550.

Figure 6A:
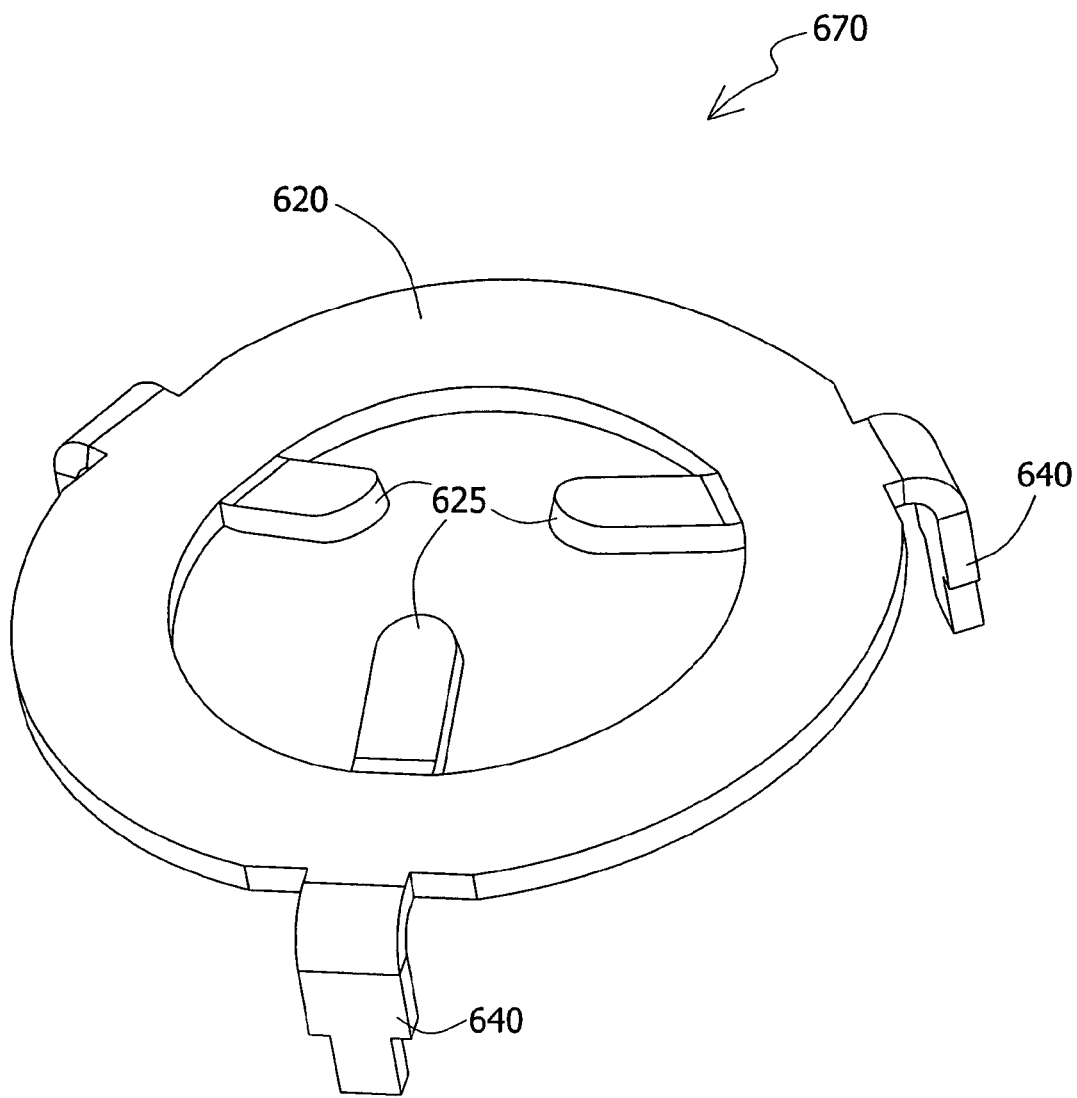
FIG. 6A schematically illustrates a three-dimensional view of a battery contact, in accordance with some embodiments of the present invention.
Figure 6B:
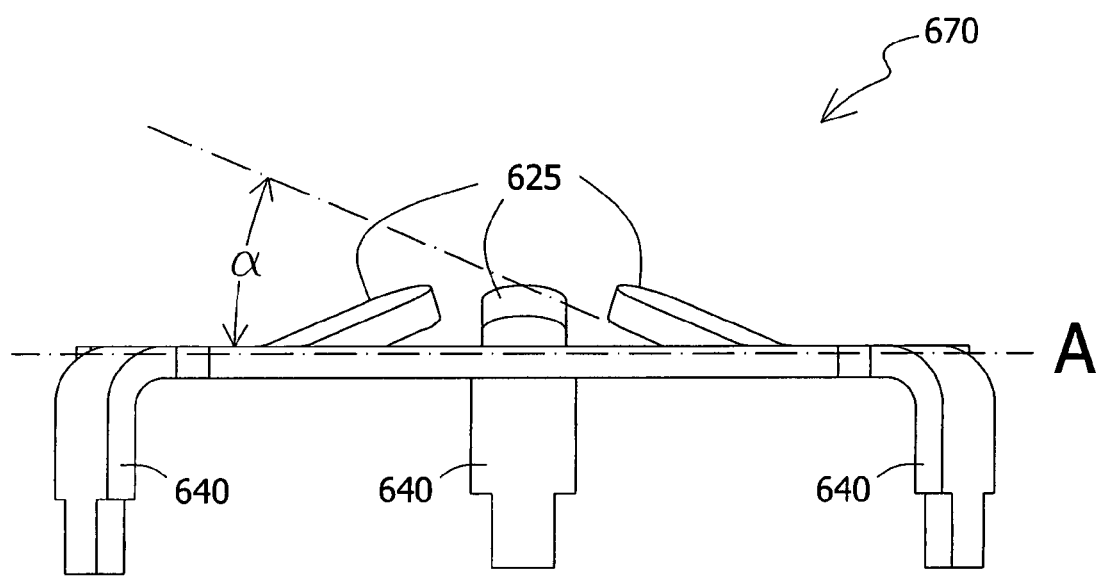
FIG. 6B schematically illustrates a side view of a battery contact, in accordance with some embodiments of the present invention.

FIGS. 6A and 6B schematically illustrate a three-dimensional view and a side view, respectively, of a battery contact 670, in accordance with some embodiments of the present invention. In some embodiments, battery contact 670 may be used in conjunction with device 340 of FIG. 3A, or with other suitable devices and systems for in vivo sensing or in vivo imaging. According to some embodiments of the present invention, the battery contact 670 may include a substrate or a support such as a ring shaped support 620. In some embodiments one or more leafs or reeds such as contact reeds 625 may be connected or may be part of the ring shaped support 620. The contact reeds 625 may be made of stainless steel and/or a conductive coating e.g. gold plating. The contacts reeds 625 may be pushed or shifted, upwards e.g. above the support 620 at an angle α (in relation to a latitude axis A) and may be in contact or hold a power support such as battery 345. The battery contact may include one or more legs, such as legs 640, which may be used to connect or attach the battery contact 670 to a circuit board such as the circuit board 350.

Figure 7:
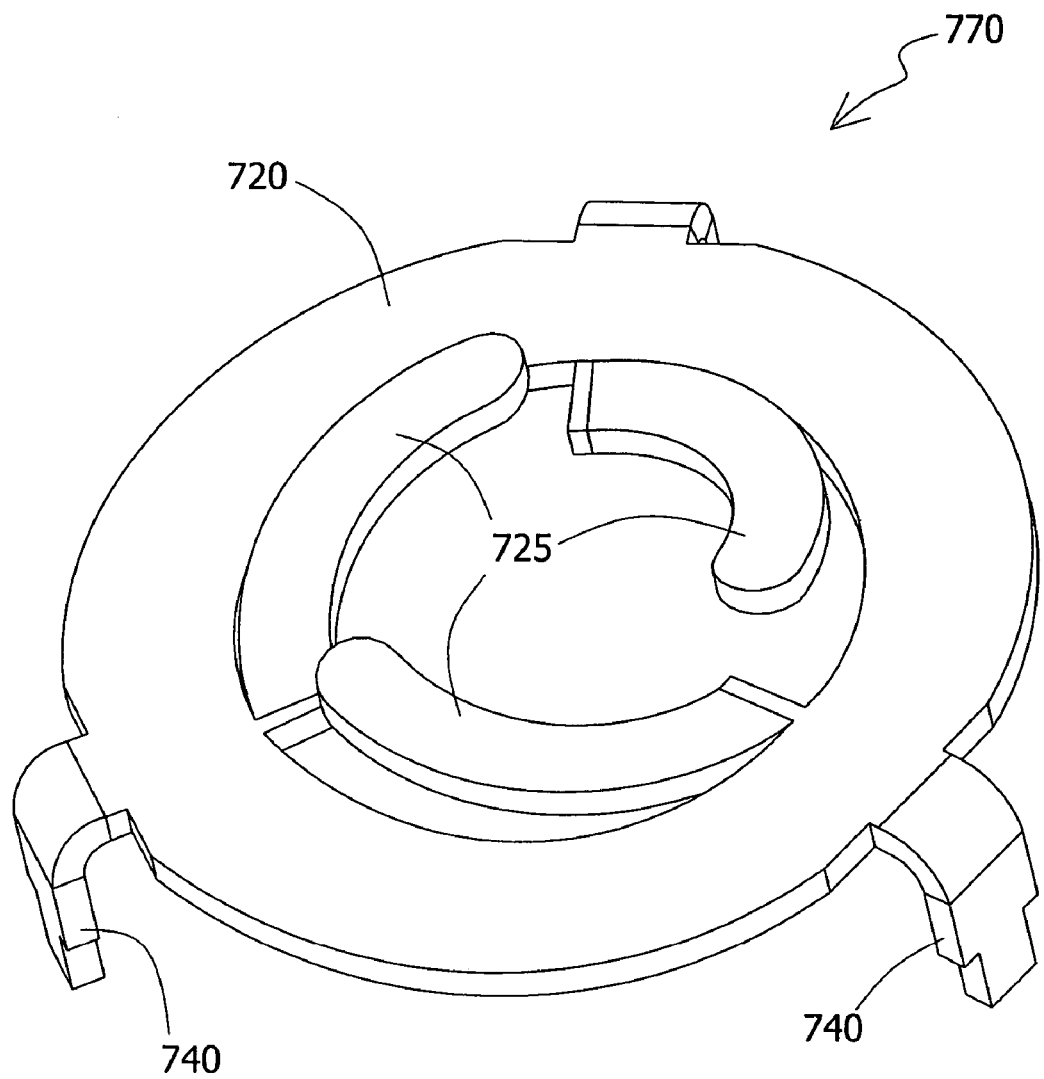
FIG. 7 schematically illustrates a three-dimensional view of a battery contact, in accordance with another embodiments of the present invention.

Reference is now made to FIG. 7, which is a schematic diagram illustrating a battery contact 770 of an in-vivo imaging device such as device 40, according 15, to some embodiments of the present invention. In some embodiments, battery contact 770 may be used in conjunction with device 340 of FIG. 3A, or with other suitable devices and systems for in vivo sensing or in vivo imaging. According to some embodiments of the present invention, the battery contact 770 may include a substrate or a support such as a ring shaped support 720. In some embodiments one or more leafs or reeds such as 'boomerang' shaped reeds 725 may be connected or may be part of the ring shaped support 720. The contact reeds 725 may be made of stainless steel and/or a conductive coating e.g. gold plating. The contacts reeds 725 may be pushed or shifted, upwards e.g. above the support 720 and may be in contact or hold a power support such as battery 345. The battery contact may include one or more legs, such as legs 740, which may be used to connect or attach the battery contact 770 to a circuit board such as circuit board 350.

It should be appreciated that the term "battery contact" may include any conductive element suitable for maintaining electrical contact between components of an in vivo imaging device, preferably a capsule endoscope.

Figure 8:
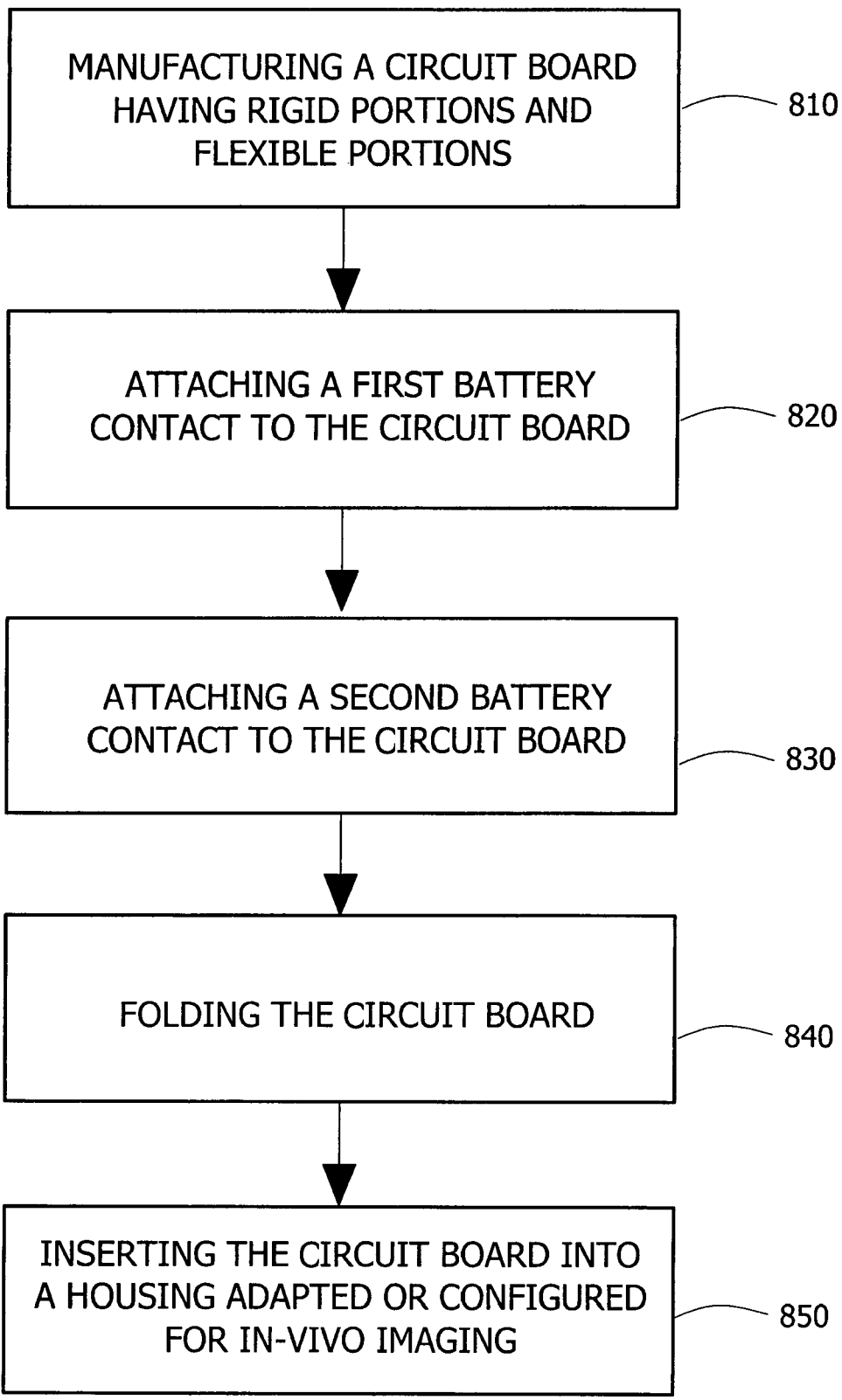
FIG. 8 is a schematic flow-chart of a method of manufacturing an in vivo imaging device with one or more battery contacts, in accordance with some embodiments of the invention.

FIG. 8 is a schematic flow-chart of a method of manufacturing an in vivo imaging device with one or more battery contacts, in accordance with some embodiments of the invention. In step 810 a circuit board having, for example rigid portions and flexible portions is manufactured. In step 820 a first battery contact such as a spring may be attached, connected or embedded to the circuit board. For example, a first battery contact e.g. battery contact 260 may be attached to rigid portion 253 of circuit board 250. In step 830 a second battery contact such as a push-button contact, a 'pin button and spring' contact or a spring biased plunger contact, a wire contact or a thin-sheet strip contact may be attached, connected or embedded to the circuit board. For example, a second battery contact e.g. battery contact 270 or battery contact 570 may be attached, respectively, to rigid portion 251 of circuit board 250, or rigid portion 551 of circuit board 550. In step 840 the circuit board e.g. and the first and second battery contacts may be folded, bended, twisted and/or shaped, for example, into a pre-defined shape. In step 850, the circuit board may be inserted into a suitable housing adapted or configured for in vivo imaging, for example, a housing of a swallowable capsule. According to one embodiment an imager may be attached or embedded to the circuit board. Other suitable operations or methods may be used in accordance with embodiments of the invention.

It will be appreciated by persons skilled in the art that the present invention is not limited to what has been particularly shown and described hereinabove. Rather, the scope of the present invention is defined by the claims which follow.

What is claimed is:

1. An in vivo device, said device comprising:
a first support having thereon a first battery contact;
a second support having thereon a second battery contact;
a battery disposed between the first support and the second support such that the battery is in contact with the first battery contact and with the second battery contact, wherein the first battery contact is a spring and the second battery contact comprises a pin to contact the battery and a housing for said pin; and
a battery stopper placed between said battery and said first or second support;
wherein the in vivo divice is an in vivo imaging device.

2. The device according to claim 1, wherein the battery stopper is placed on the second support.

3. The device according to claim 1, wherein the first support and second support are printed circuit boards.

4. The device according to claim 2, wherein when assembled, the second battery contact allows for space between the battery and the second support, said second support having at least one component disposed thereon, said component being within said space.

5. The device according to claim 1, wherein said first support has thereon at least one component selected from the list consisting of an imager, an optical system and an illumination source.

6. The device according to claim 1, wherein said second support has disposed thereon an antenna.

7. The device according to claim 4, wherein said component comprises a transmitter/receiver.

8. The device according to claim 4, wherein said component comprises a switch.

9. The device according to claim 1, wherein said first and second supports are connected by a flexible portion.

10. The device according to claim 1, wherein said device is capsule shaped.

11. An in vivo device comprising:
two optical domes and a connecting sleeve to connect the optical domes,
wherein the connecting sleeve comprises therein:
a first support having thereon a first battery contact;
a second support having thereon a second battery contact;
and wherein the connecting sleeve comprises a battery stopper and the in vivo device is an in vivo imaging device.

12. The device according to claim 11, wherein the first battery contact is a spring and the second battery contact comprises a pin to contact the battery and a housing for said pin.

13. The device according to claim 11, wherein the second support has disposed thereon at least one component of the device.

14. The device according to claim 11, wherein the first support and second support are printed circuit boards.

15. The device according to claim 13, wherein when assembled with a battery disposed between the first support and the second support such that the battery is in contact with the first battery contact and with the second battery contact, the second battery contact allows for space between the battery and the second support, said component disposed on said second support being within said space.

16. The device according to claim 11, wherein said first support has disposed thereon at least one component selected from the list consisting of an imager, an optical system and an illumination source.

17. The device according to claim 11, wherein said second support has disposed thereon an antenna.

18. The device according to claim 13, wherein said component comprises a transmitter/receiver.

19. The device according to claim 13, wherein said component comprises a switch.

20. The device according to claim 11, wherein said first and second supports are connected by a flexible portion.

21. The device according to claim 11, wherein said device is capsule shaped.

* * * * *